(12) United States Patent
Saadat et al.

(10) Patent No.: US 8,016,750 B2
(45) Date of Patent: Sep. 13, 2011

(54) FLEXIBLE TUBULAR LINER COATING SYSTEM

(75) Inventors: Vahid Saadat, Atherton, CA (US); Arvin T. Chang, West Covina, CA (US)

(73) Assignee: USGI Medical, Inc., San Clemente, CA (US)

( * ) Notice: Subject to any disclaimer, the term of this patent is extended or adjusted under 35 U.S.C. 154(b) by 186 days.

(21) Appl. No.: 12/426,900

(22) Filed: Apr. 20, 2009

(65) Prior Publication Data

US 2009/0209814 A1 Aug. 20, 2009

Related U.S. Application Data

(63) Continuation of application No. 11/245,538, filed on Oct. 6, 2005, now Pat. No. 7,520,950.

(51) Int. Cl.
*B31D 3/04* (2006.01)
(52) U.S. Cl. .......... 600/121; 600/101; 428/34.1
(58) Field of Classification Search .......... 600/101, 600/121; 428/34.1
See application file for complete search history.

(56) References Cited

U.S. PATENT DOCUMENTS

| | | |
|---|---|---|
| 3,515,579 A | 6/1970 | Shepard et al. |
| 4,563,231 A | 1/1986 | Porrmann et al. |
| 4,643,788 A | 2/1987 | Hashimoto |
| 5,413,645 A | 5/1995 | Saunders et al. |
| 5,451,460 A | 9/1995 | Lu et al. |
| 6,120,634 A | 9/2000 | Harrold et al. |
| 2003/0233066 A1 | 12/2003 | Ewers et al. |
| 2005/0250990 A1 | 11/2005 | Le et al. |

*Primary Examiner* — Jeff Aftergut
*Assistant Examiner* — Jaeyun Lee
(74) *Attorney, Agent, or Firm* — Levine Bagade Han LLP

(57) ABSTRACT

Flexible tubular liner coating systems are described herein. A method for coating and forming the flexible tubular inner liner may comprise, in one example, coating at least a first surface of a flexible elongate strip having a first and a second edge and then bringing the first and second edges of the flexible elongate strip into proximity of one another. Once the edges are brought towards one another, they may be joined such that a flexible tubular liner is formed having the coated first surface formed as an inner surface of the flexible tubular liner. Flexible tubular liner coating systems are described herein. A method for coating and forming the flexible tubular inner liner may comprise, in one example, coating at least a first surface of a flexible elongate strip having a first and a second edge and then bringing the first and second edges of the flexible elongate strip into proximity of one another. Once the edges are brought towards one another, they may be joined such that a flexible tubular liner is formed having the coated first surface formed as an inner surface of the flexible tubular liner.

24 Claims, 8 Drawing Sheets

FLEXIBLE TUBULAR LINER COATING SYSTEM

CROSS-REFERENCE TO RELATED APPLICATIONS

This application is a continuation of U.S. application Ser. No. 11/245,538 filed Oct. 6, 2005, now U.S. Pat. No. 7,520,950, issued Apr. 21, 2009, which is incorporated by reference in its entirety.

BACKGROUND OF THE INVENTION

Field of the Invention

The present invention relates to systems for coating and forming a flexible tubular liner for use in an elongate instrument. More particularly, the present invention relates to systems for coating and forming a thin-wall flexible tubular liner from flat strips for use in an elongate instrument.

The use of the endoscope for examining the interior of the intestinal tract is well-known. A complete examination typically requires the physician to advance the endoscope into the colon, negotiate the sigmoid colon, and left and right colic flexures up to the cecum. Other previously-known apparatus and methods use an overtube having variable rigidity, so that the overtube may be inserted through curved anatomy in a flexible state, and then selectively stiffened to resist bending forces generated by passing a colonoscope through the overtube.

Once the procedure is finished, the endoscope or overtube is typically sterilized for reuse in another patient. One method for maintaining sterility of the instrument involves positioning an inner liner within a working lumen of the instrument and an outer liner over an outer surface of the instrument such that the device is completely encapsulated and prevented from directly contacting a patient. The inner liner, in particular, is typically covered with a coating, e.g., a hydrophilic coating, over its inner surface to facilitate the passage of tools or instruments through the liner.

However, manufacturing and coating thin-walled tubular liners which are flexible is particularly difficult. Such liners can be typically extruded from a polymeric material to a desired length; however, applying a coating to the liner, particularly over its inner surface, is made difficult by the liner's inability to maintain a tubular structure because of its thin-wall and flexibility requirements. The difficulty of coating the liner inner surface is further compounded by the inability of such a liner to maintain its tubular structure during curing or drying of the coating material upon the liner inner surface.

Accordingly, there exists an un-met need for methods and devices to facilitate the manufacturing and coating of thin-wall tubular liners.

BRIEF SUMMARY OF THE INVENTION

Overlying a linked shapelocking body is a liner or covering assembly having an inner liner or layer, which extends through a main lumen of the linked body, and an outer liner or layer. The inner liner may extend from a distal tip and proximally through a handle assembly to terminate externally of or at an entry lumen. The inner liner may typically be made from a soft elastomeric and/or hydrophilic coated material, such as silicon or synthetic rubber. The inner liner extends through the elongate body lumen and can be coated, e.g., with a hydrophilic material, to facilitate the passage of instruments, e.g., an endoscope, through the lumen over the inner liner by increasing the surface lubricity and reducing its coefficient of friction to thereby reduce friction between the instrument and the inner surface of the inner liner, especially when a fluid such as water, saline, etc., is applied to the hydrophilic material.

A method for coating and forming the flexible tubular inner liner may comprise, in one example, coating at least a first surface of a flexible elongate strip having a first and a second edge and then bringing the first and second edges of the flexible elongate strip into proximity of one another. Once the edges are brought towards one another, they may be joined such that a flexible tubular liner is formed having the coated first surface formed as an inner surface of the flexible tubular liner.

One example for a manufacturing assembly process for coating and forming the inner liner may comprise having a liner cartridge containing a roll of flat strip of liner material feed the flat strip through a number of pinch rollers. As the flat strip is passed through assembly process, an inner liner surface may be coated with a hydrophilic material using, e.g., a coating sprayer, which sprays the coating through a nozzle onto the liner surface. Other coating methods and devices may be utilized, such as dipping through a coating bath, etc.

Moreover, both surfaces of the strip may also be coated as well. Coating the outer surface of the tubular liner to be formed may additionally facilitate the loading of the inner liner through the shapelock lumen by reducing the frictional contact between the outer surface of the inner liner and the links of shapelock body without comprising the bending or flexible characteristics of the inner liner. The range of hydrophilic coating materials dispensed upon the liner surface may include a number of different hydrophilic materials, e.g., polyvinylpyrrolidone (PVP or PVNP), polyhydroxethyl-methacrylate (PHEMA) hydrogels, polyvinylalcohol (PVA), polyethylene oxide (PEO), polycarboxylic acids (PCA), polymethyacrylic (PMMA), etc.

After the liner flat strip has been sprayed, dipped, or otherwise coated, the flat strip continues through the assembly process where the applied coating may be activated via a lamp, such as a heat or ultraviolet lamp. The lamp may be directed to a single surface or to both sides of the strip if coating material is present on both sides of the strip. Once the coating material is activated, the strip may be cured at room temperature or it may be passed through an oven via an oven opening to cure or dry the coating material upon the strip anywhere from several minutes to hours, depending upon the characteristics of the coating material.

The flat strip exiting the oven having the hydrophilic coating material thereupon may then be formed into its tubular structure by forming the strip over a mandrel assembly. As the strip continues to be pulled through the assembly process, a series of rollers, e.g., bottom rollers, top roller, and side rollers, positioned to rotate adjacent to mandrel assembly brings the free side edges of the strip towards one another over the mandrel for joining. The top roller may compress or otherwise join the approximated edges together along a joined seam to produce a formed tubular liner having the desired coating characteristics. Once the tubular liner has been sufficiently drawn, it may be cut to length as desired.

DETAILED DESCRIPTION OF THE INVENTION

Generally in use, an endoscope may be advanced into a patient's body lumen, such as the lower gastro-intestinal tract via the anus or the upper gastro-intestinal tract via the patient's mouth. However, the tissue of the colon and small intestines are typically unsupported and advancement through these body lumens is difficult. Furthermore, looping of the tissue and unraveling of pleated tissue relative to the endoscope makes endoscopic advancement particularly difficult. Accordingly, providing a stable platform through which the endoscope may be endoluminally advanced may facilitate the endoluminal manipulation of the endoscope and examination of the tissue.

Figure 1:
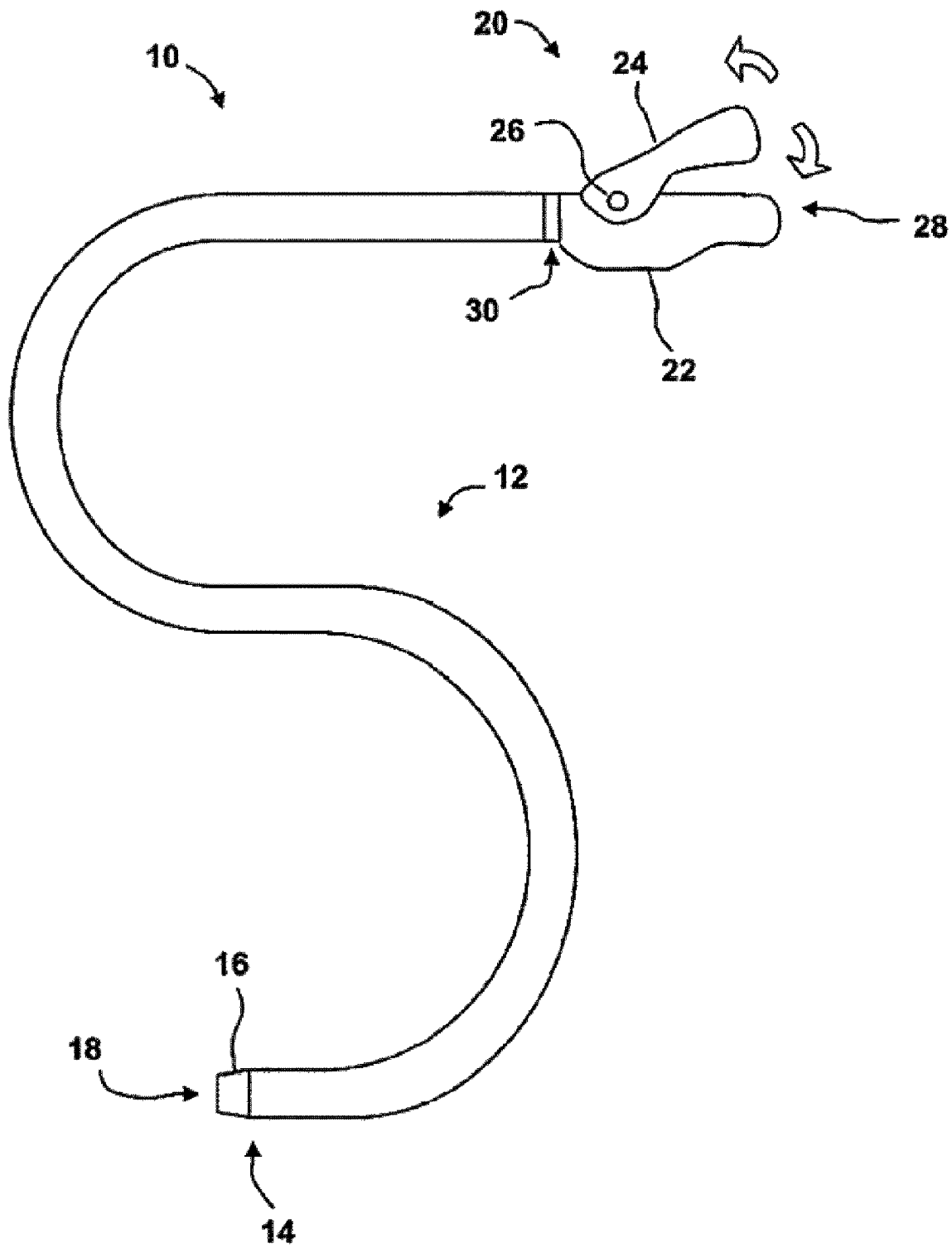
FIG. 1 illustrates a shapelock assembly defining at least one lumen therethrough.

An example of a stable endoluminal platform device is shown in shapelock assembly 10 in FIG. 1. Shapelock assembly 10 may generally comprise an elongate body 12 which defines at least one lumen 18 therethrough for advancement of an endoscope or other endoscopic instruments therethrough. A distal tip 16, which may be configured into an atraumatic shape, may be positioned near or at the distal end 14 of elongate body 12. Handle assembly 20 may be coupled to a proximal end of elongate body 12.

Handle assembly 20 may be comprised generally of handle body 22 and locking handle 24 which may be configured to actuate one or more cables routed throughout elongate body 12 such that a plurality of nested links, in part comprising body 12 and as described below in further detail, are compressed against one another to transition elongate body 12 from a flexible state to a rigid shape-locked state. Once in its shape-locked condition, elongate body 12 maintains any configuration in a rigid manner. Release of locking handle 24 relative to handle body 22 releases elongate body 12 to transition back into a flexible body to conform into another configuration.

Locking handle 24 may be rotatably coupled to handle body 22 via pivot 26 such that rotation of locking handle 24 in the direction shown in FIG. 1 against handle body 22 may actuate the shape-locking feature of elongate body 12. However, any number of actuation mechanisms as generally known may also be utilized. Handle body 22 may also define in its proximal end an entry lumen 28 which extends through handle assembly 20 and elongate 10 body 12. The proximal end of elongate body 12 may be coupled or otherwise attached to handle assembly 20 at handle interface 30. As mentioned above, an endoscope or any number of endoscopic instruments may be advanced into and through entry lumen 28 and elongate body 12 to effect treatment through assembly 10. Further details and examples of shape-locking elongate bodies are disclosed in U.S. patent application Ser. No. 10/281,462 filed Oct. 25, 2002 (U.S. Pat. Pub. No. 2003/0233066 A1), which is incorporated herein by reference in its entirety.

Figure 2:
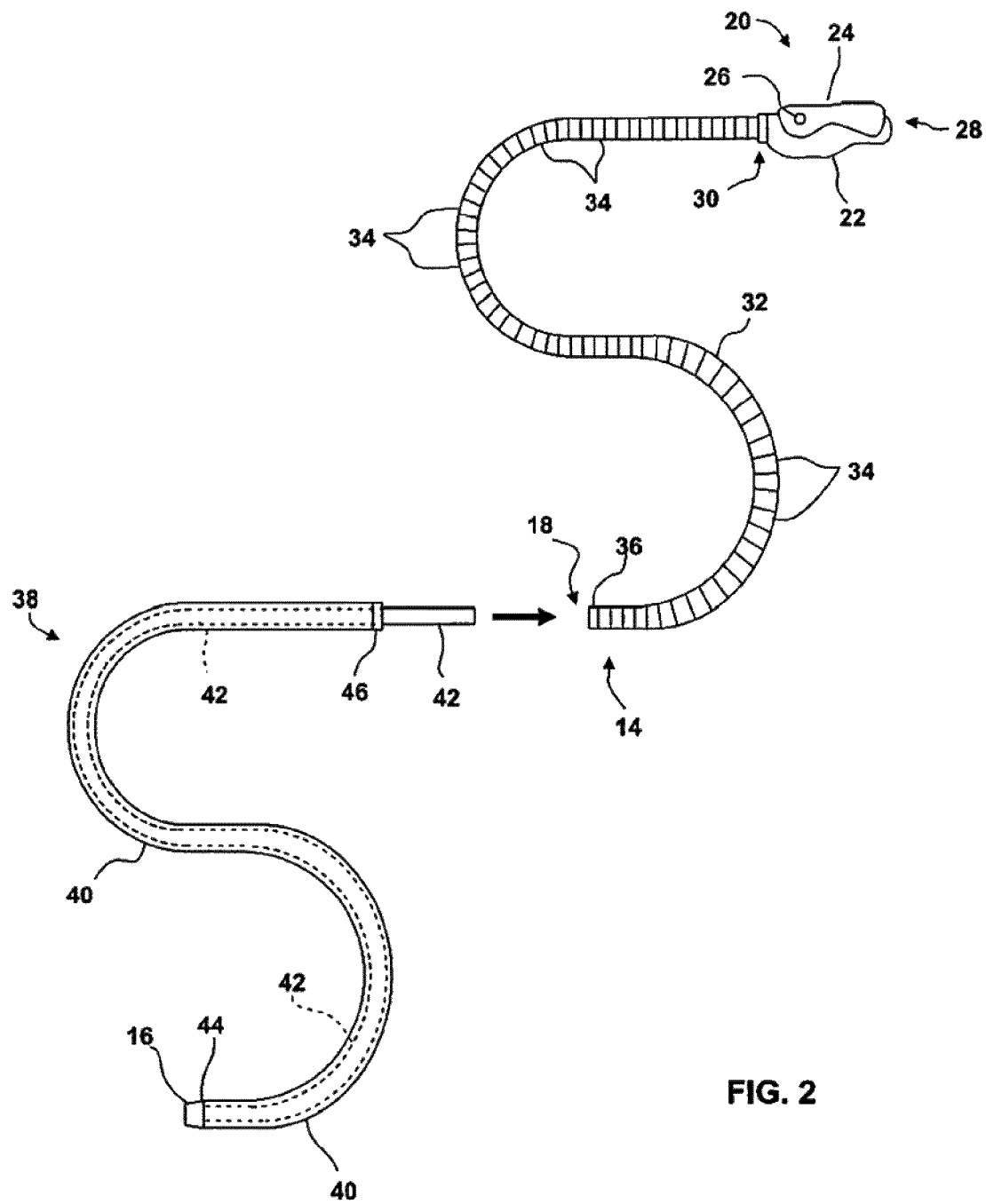
FIG. 2 illustrates an assembly view of an exposed elongate shapelocking body and a liner assembly which may be disposed upon and within the elongate body.

As mentioned above and as shown in FIG. 2, the shape-locking elongate body 12 is generally comprised of an underlying body 32 having a plurality of nested links 34 which are slidable relative to one another. Each link 34 may define one or more openings therethrough 20 such that the stacked links 34 collectively form lumen 18 through the length of the device. The terminal link 36 positioned near or at the distal end of the link body 32 may anchor one or several control wires which are routed through the length of body 32. Overlying the linked body 32 is a liner or covering assembly 38. An inner liner or layer 42 may typically comprises a soft elastomeric and/or hydrophilic coated material, such as silicon or synthetic rubber, and extends through lumen 18 of nestable links 34 to a liner for the lumen 18. Inner liner 42 may extend from distal tip 16 and proximally through handle assembly 20 to terminate externally of or at entry lumen 28.

An outer liner 40, which may be formed into a flexible elastomeric covering, may also extend from distal tip 16 over inner liner 42 such that outer and inner liners 40, 42 may be integrally formed with one another in attachment 44 at distal tip 16. When inner liner 42 is positioned within lumen 18 and outer liner 40 is disposed over body 32 to encapsulate the links 34, the proximal end of outer liner 40 may be connected or otherwise attached, e.g., via a temporary mechanical connection. via handle locking interface 46 at the proximal end of outer liner 40 to handle interface 30. Outer liner 40. when disposed over links 34. provides a relatively smooth outer surface for elongate body 12 and aids in preventing tissue from being captured or pinched during relative rotation of adjacent nestable links 34. Further examples and descriptions of the liner assembly 38 and its positioning upon the shape-locking assembly may be seen in further detail in U.S. patent application Ser. No. 11/115,947 filed Apr. 26, 2005, which is incorporated herein by reference in its entirety.

As previously mentioned, inner liner 42 extends through lumen 18 and can be coated. e.g.•with a hydrophilic material, to facilitate the passage of instruments, e.g., an endoscope, through lumen 18 over inner liner 42 by increasing the surface lubricity and reducing its coefficient of friction to thereby reduce friction between the instrument and the inner surface of inner liner 42, especially when a fluid such as water. saline, etc., is applied to the hydrophilic material. The inner liner 42 wall thickness may typically range between 0.15 mm to 0.40 mm and the inner liner inner diameter may typically range between 4 mm to over 15 mm to accommodate various size instruments passed therethrough. An inner liner 42 may be extruded directly into its tubular structure but due to the thin-wall and flexible nature of the liner material, applying a hydrophilic coating having a thickness of less than 0.025 mm onto, e.g., the inner surface of inner liner 42, is difficult.

Accordingly, a flattened strip may be first dipped. sprayed. or otherwise coated with the hydrophilic material and then rolled or manipulated into a tubular structure to form the inner liner 42. Once the coated inner liner 42 has been formed, it may be cut to an appropriate length and joined with the outer liner 40 to form the liner assembly 38 for use with shapelock assembly 10.

Figure 3A:
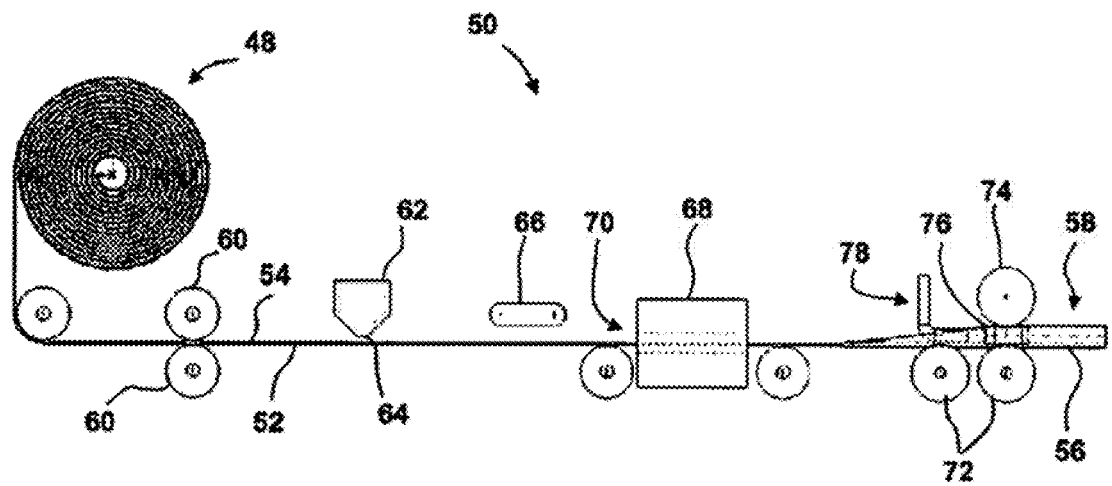
FIGS. 3A and 3B show side and perspective schematic views, respectively, of an example for coating and forming a tubular liner from a flat strip of material.
Figure 3B:
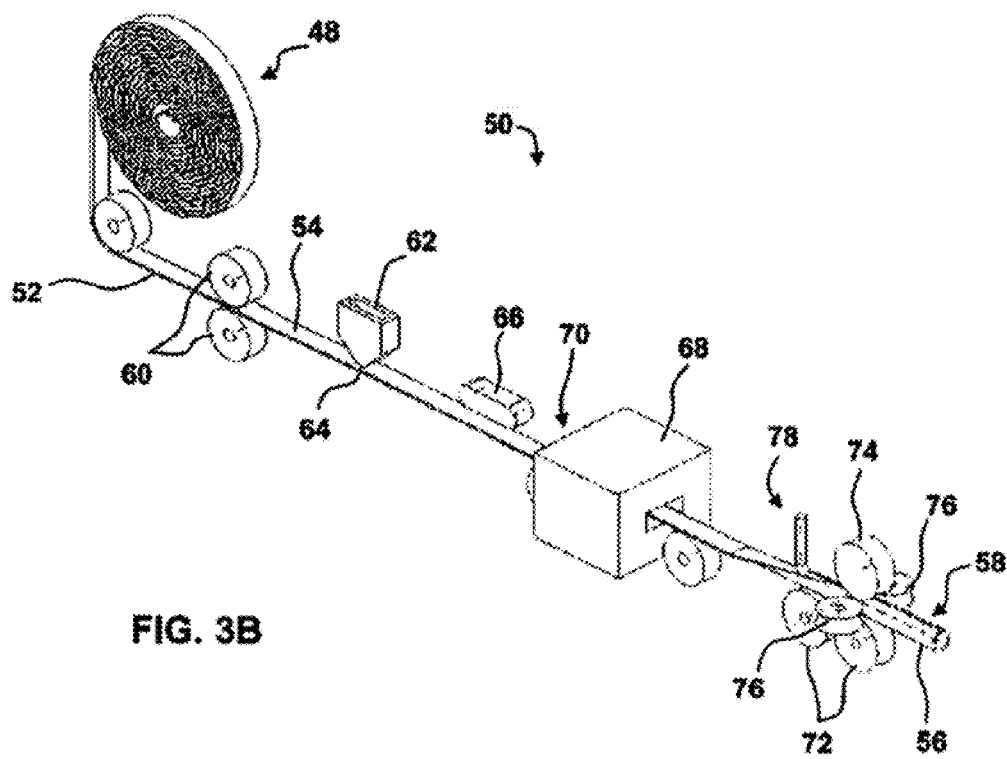

One example for a manufacturing assembly process 50 for coating and forming the inner liner may be seen in the schematic side and perspective illustrations of FIGS. 3A and 3B. respectively. A liner cartridge 48 containing a roll of flat strip of liner material may feed a flat strip 52 of liner material through a number of pinch rollers 60. As the flat strip 52 is passed through assembly process 50, an inner liner surface 54 may be coated with a hydrophilic material using, e.g. a coating sprayer 62. which sprays the coating through a nozzle 64 onto the liner surface 54. Although a sprayer 62 is illustrated dispensing material on a single surface of the flat strip 52. other coating methods and devices may be utilized such as dipping through a coating bath, etc.

Moreover, although the example illustrates coating on a single surface of flat strip 52, both surfaces of the strip 52 may also be coated as well. Coating the outer surface of the tubular liner to be formed may additionally facilitate the loading of the inner liner 42 through the shapelock lumen 18 by reducing the frictional contact between the outer surface of inner liner 42 and the links of shapelock body 32 without comprising the bending or flexible characteristics of inner liner 42. The range of hydrophilic coating materials dispensed upon liner surface 54 may include a number of different hydrophilic materials, e.g., polyvinylpyrrolidone (PVP or PVNP), polyhydroxethylmethacrylate (PHEMA) hydrogels, polyvinylalcohol (PVA), polyethylene oxide (PEO), polycarboxylic acids (peA), polymethyacrylic (PMMA), etc.

After the liner flat strip 52 has been sprayed, dipped, or otherwise coated, the flat strip 52 continues through the assembly process 50 where the applied coating may be activated via a lamp 66, such as a heat or ultraviolet lamp. Lamp 66 may be directed to a single surface 54 or to both sides of strip 52 if coating material is present on both sides of strip 52. Once the coating material is activated, strip 52 may be cured at room temperature or it may be passed through oven 68 via oven opening 70 to cure or dry the coating material upon strip 52 anywhere from several minutes to hours, depending upon the characteristics of the coating material.

The flat strip 52 exiting oven 68 having the hydrophilic coating material thereupon may then be formed into its tubular structure by forming the strip 52 over a mandrel assembly 78. As strip 52 continues to be pulled through assembly process 50, a series of rollers, e.g., bottom rollers 72, top roller 74, and side rollers 76, positioned to rotate adjacent to mandrel assembly 78 brings the free side edges of strip 52 towards one another over mandrel 78 for joining. Top roller 74 may compress or otherwise join the approximated edges together along a joined seam 58 to produce a formed tubular liner 56 having the desired coating characteristics. Once tubular liner 56 has been sufficiently drawn, it may be cut to length as desired.

Figure 4:
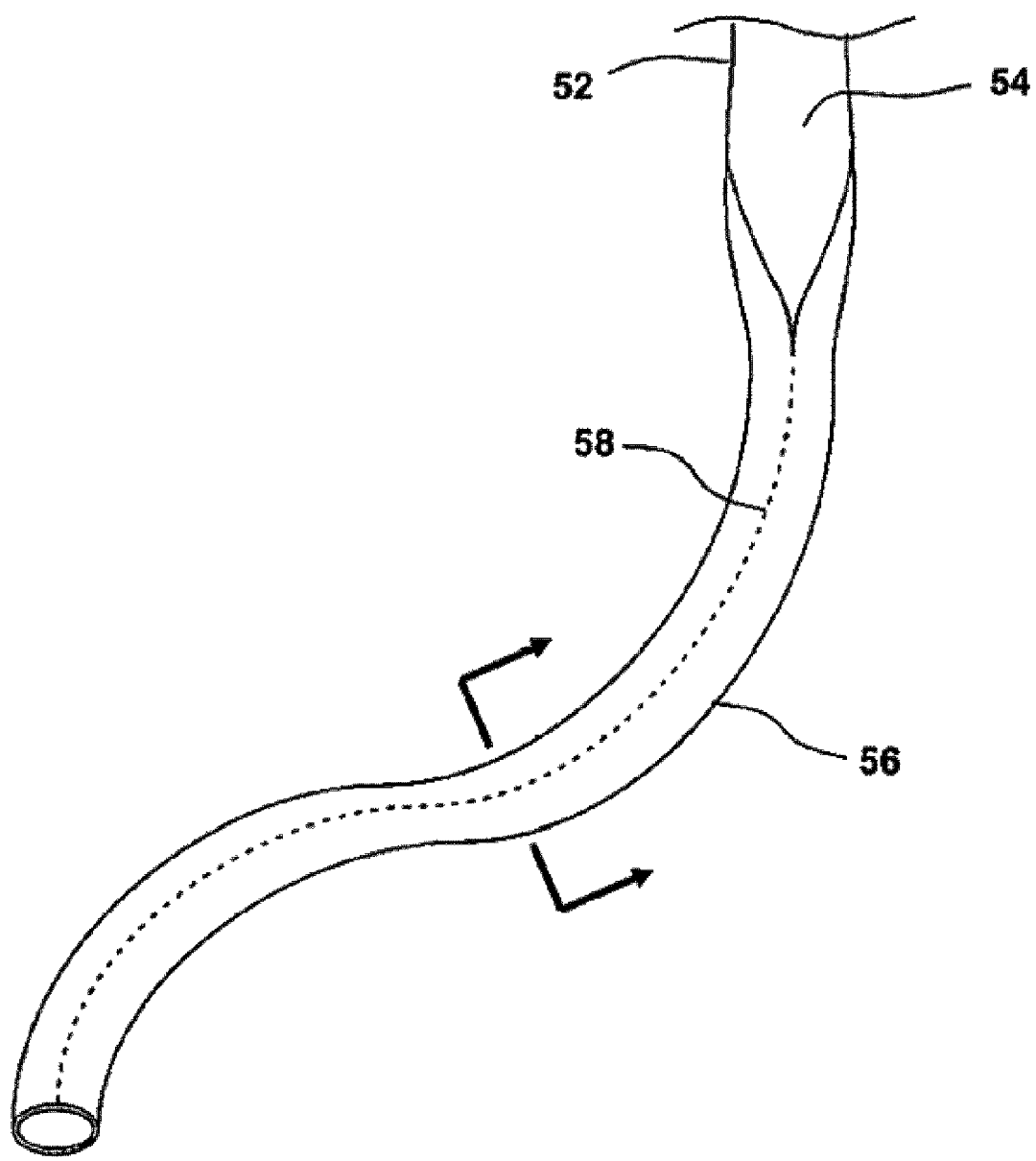
FIG. 4 illustrates an example of a partial tubular liner formed and coated from a flat strip.

FIG. 4 shows an illustrative view of a partially formed tubular liner 56 which has been joined along seam 58. The transition from flat strip 52 to tubular liner 56 may be seen where the free edges of strip 52 have been approximated towards one another and joined along seam 58. As shown, the coated surface 54 of flat strip 52 may become the inner surface of tubular liner 56.

Figure 5A:
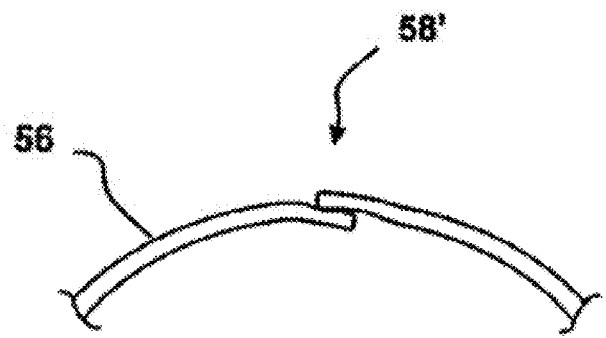
FIGS. 5A to 5C show partial cross-sectional views of some illustrative liner-forming examples respectively utilizing lap joints, butt joints, and adhesives.
Figure 5B:
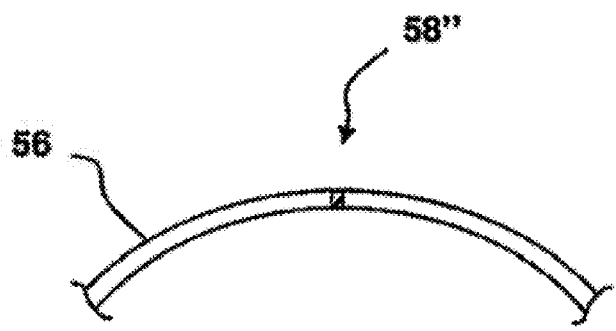
Figure 5C:
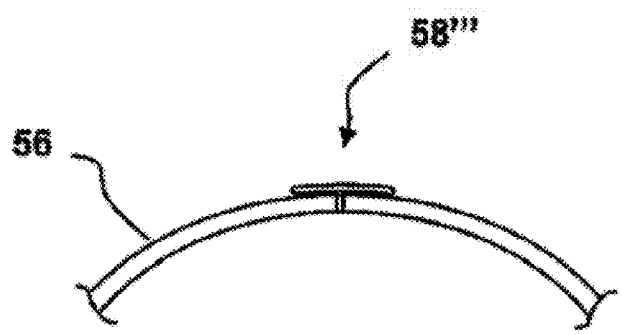

FIGS. 5A to 5C show a partial cross-sectional detail view of various examples for joining the edges of strip 52 along seam 58. FIG. 5A shows a variation where the edges of tubular liner 56 may be joined in a lap joint 58' by applying an adhesive between the edges of the joint 58' or by thermally fusing the edges to one another. FIG. 5B shows another variation where the edges of tubular liner 56 may be attached to one another in a butt joint 58" again utilizing an adhesive or by thermally fusing the edges. In yet another variation, the edges of tubular liner 56 may be attached to one another via a film or tape 58''' overlying the free edges, e.g., a polymeric adhesive film such as Kapton® (DuPont, Circleville, Ohio). Although these examples illustrate specific types of joints or seams, these are intended to be illustrative of the types of joining mechanisms and are intended to include any number of other known methods.

Figure 6:
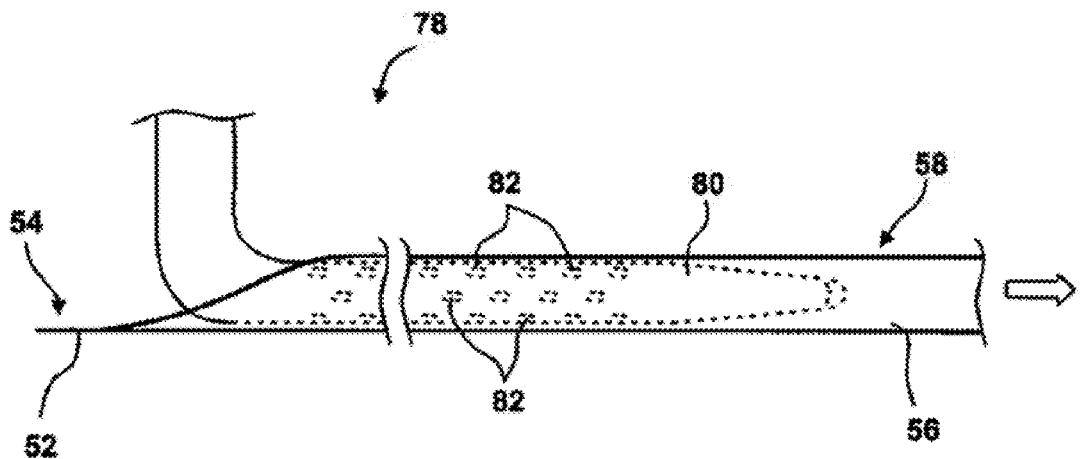
FIG. 6 shows one variation of a mandrel fluidly coupled to a vacuum about which the flexible tubular liner may be formed.

In creating a seam 58 joining the free edges of flat strip 52 into tubular liner 56, different methods may be employed. In one variation, mandrel assembly 78 may have an elongate member 80 about which flat strip 52 is formed about, as shown in FIG. 6. The elongate member 80 may have an optionally tapered distal end to prevent tearing or nicking of tubular liner 56 against member 80 and it may also optionally define one or more openings 82 over its surface. Openings 82 may be in fluid communication through a common channel defined through elongate member 80 and fluidly coupled to a vacuum source (not shown) which may be used to draw the flat strip 52 directly against the outer surface of elongate member 80 so as to securely hold or maintain a position of the free edges of flat strip 52 relative to one another when forming seam 58.

Figure 7:
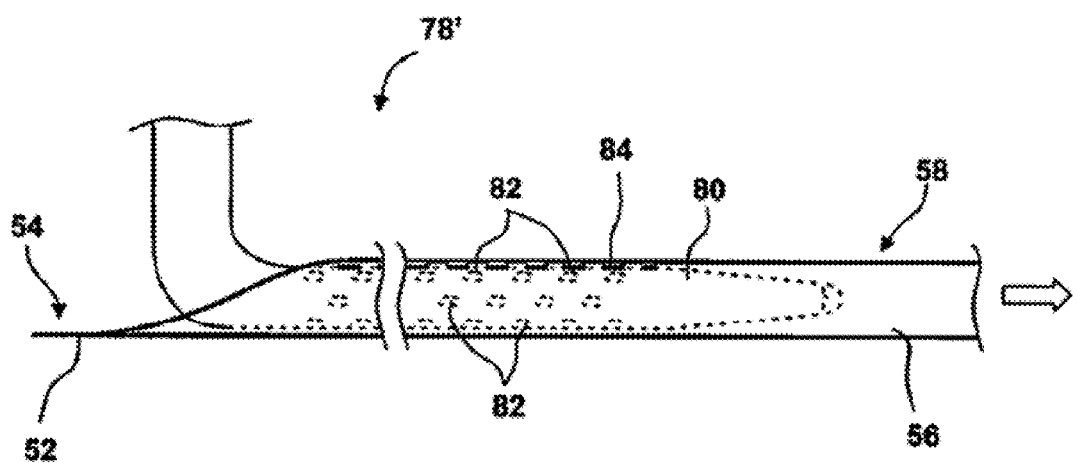
FIG. 7 shows another variation of a mandrel utilizing a longitudinal heating element, such as a wire, for adhering the free edges of the strip to one another into a tubular liner.

In a variation for forming seam 58, a heating wire or strip 84 may be integrated or positioned along a top portion of elongate member 80 such that the free edges of flat strip 52 are brought into proximity to or directly upon heating wire or strip 84, as shown in FIG. 7. Heating wire or strip 84 may be made from a variety of electrically resistive materials, e.g., nichrome, steel, platinum, etc., which are insulated from the underlying elongate member 80. With strip 52 held against elongate member 80, e.g., via a vacuum created through openings 82, heating wire or strip 84 may be energized to melt or fuse the free edges into seam 58 to form tubular liner 56. The flat strip 52 and the assembly process may be halted intermittently to allow the formation of seam 58; alternatively, tubular liner 56 may be urged continuously along the elongate member 80 while simultaneously forming seam 58 without having to halt the assembly process.

Figure 8:
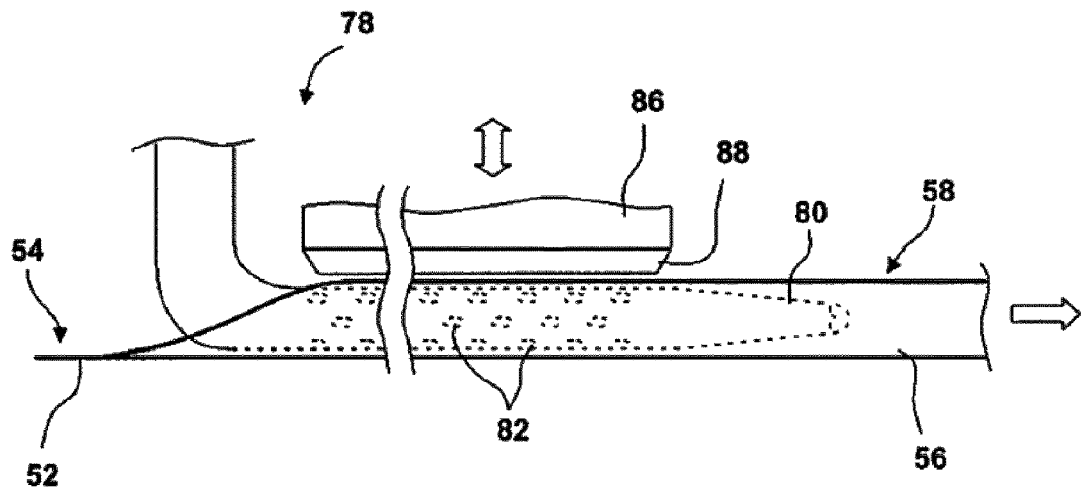
FIG. 8 shows yet another variation utilizing a movable heating element for pressing against the edges of the strip.

Mandrel assembly 78' may be fabricated from a variety of materials, e.g., metals such as stainless steel, aluminum, etc., or ceramics to provide for electrical or thermal insulation for applications where seam 58 is thermally formed. Another variation for thermally bonding or fusing strip 52 into tubular liner 56 is shown in FIG. 8 where a heating assembly 86 may be positioned adjacent to elongate member 80 for forming seam 58. Heating assembly 86 may have a heating/compression pad or strip 88 positioned directly above elongate member 80. As strip 52 passes between elongate member 80 and heating assembly 86, heating/compression strip 88 may be heated to fuse the underlying strip 52 into seam 58. Alternatively, heating assembly 86 may be moved into direct contact temporarily against the edges of strip 52 to heat and compress the strip 52.

Figure 9:
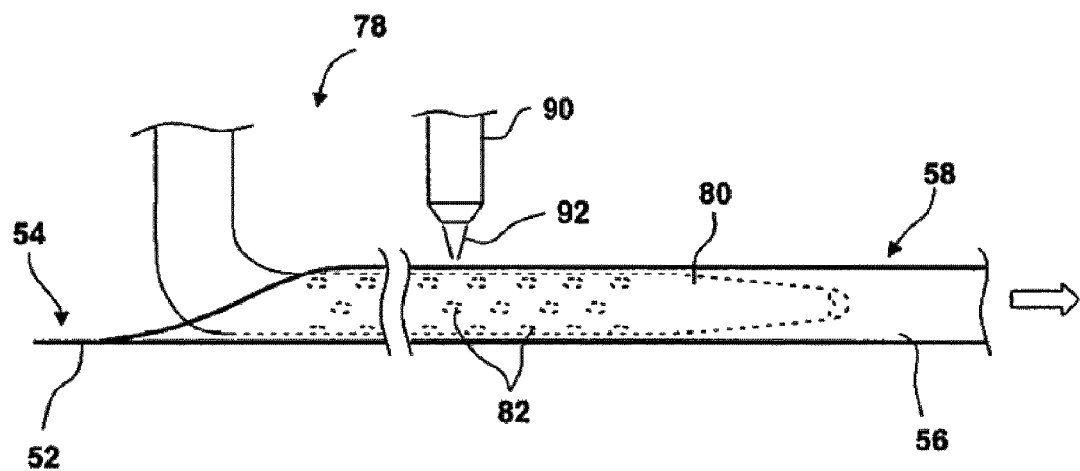
FIG. 9 shows yet another variation utilizing a spraying nozzle or laser for adhering the edges of the strip.

In yet another variation, a laser 90 may be positioned above elongate member 80 such that a beam of light 92 is directed against strip 52 to fuse seam 58, as shown in FIG. 9. Alternatively, a spraying nozzle may be positioned in place of laser 90 to direct a stream or spray of adhesive to fuse seam 58.

Figure 10A:
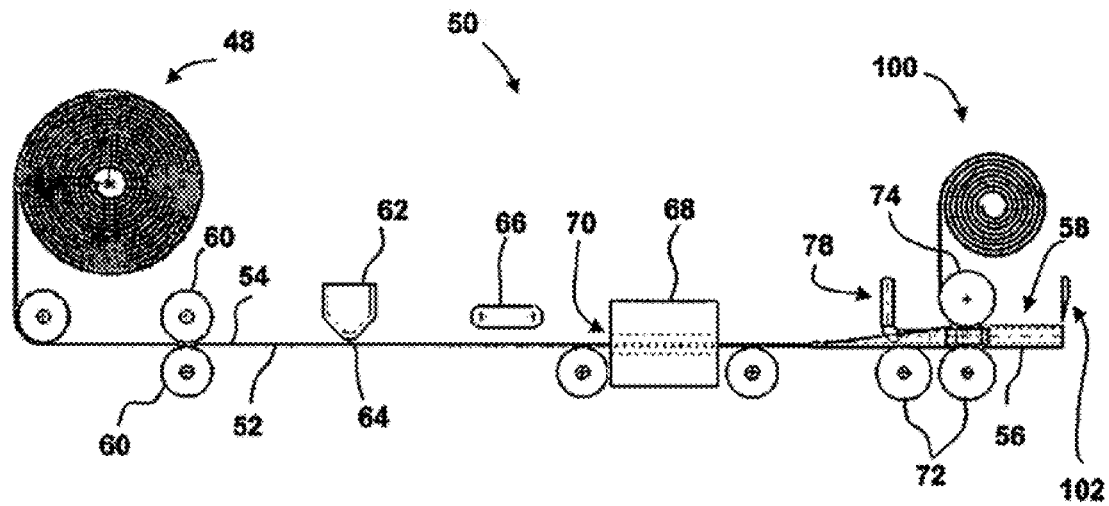
FIGS. 10A and 10B show side and perspective schematic views, respectively, of another example for coating and forming a tubular liner from a flat strip of material utilizing an adhesive strip for dispensing and adhering against the edges of the strip.
Figure 10B:
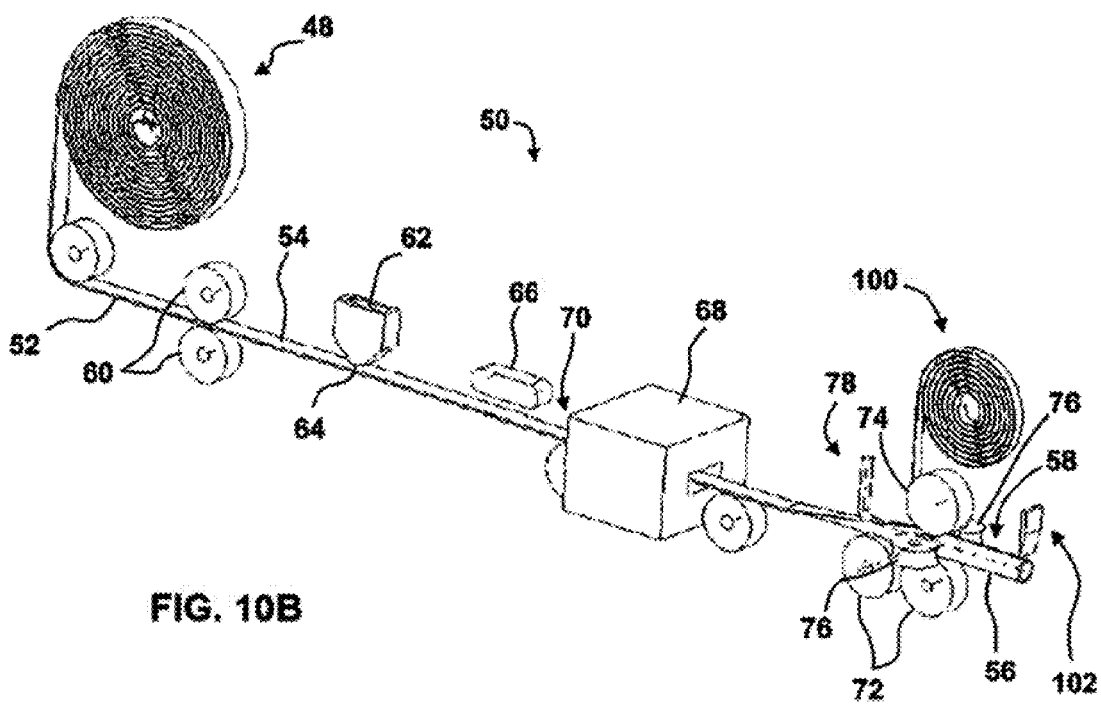

Yet another variation is shown in the schematic side and perspective illustrations of FIGS. 10A and 10B, respectively, which is similar to that shown in FIGS. 3A and 3B above. However, this variation shows an example of an integrated roll of film or tape 100, e.g., a polymeric adhesive film such as Kapton® as described-above, which may be applied directly to the free edges of strip 52 automatically by roller 74 to form tubular liner 56. Also shown is an illustrative cutting blade 102 which may be located at a distal position to sever the formed tubular liner 56 at desired lengths. The cutting blade 102 may be integrated with the assembly process 50 to be fully automated or manually operable. Moreover, cutting blade 102 is merely intended to be illustrative of a cutting or severing mechanism and may formed into any number of cutting mechanisms. Furthermore, although cutting blade 102 is illustrated in this variation, cutting blade 102 may be integrated in any of the above-described processes.

Although various illustrative variations are described above, it will be evident to one skilled in the art that a variety of combinations of aspects of different variations, changes, and modifications are within the scope of the invention. It is intended in the appended claims to cover all such combinations, changes, and modifications.

The invention claimed is:

1. An apparatus having a liner assembly prepared by a process comprising the steps of:
    coating at least a first surface of a flexible elongate strip having first and second edges;
    bringing the first and second edges of the flexible elongate strip into proximity of one another;
    joining the first and second edges such that a flexible tubular liner is formed having the coated first surface formed as an inner surface of the flexible tubular liner;
    joining said flexible tubular liner with a generally tubular outer sheath to form a liner assembly; and
    installing the liner assembly onto an elongate body having a tubular shape defining an internal lumen, wherein the tubular liner extends within the internal lumen and the outer sheath extends over an external surface of the elongate body.

2. The apparatus having a liner assembly prepared by the process comprising the steps of claim 1, wherein coating further comprises coating a second surface of the flexible elongate strip.

3. The apparatus having a liner assembly prepared by the process comprising the steps of claim 1, wherein coating comprises applying a hydrophilic material upon at least the first surface.

4. The apparatus having a liner assembly prepared by the process comprising the steps of claim 3, wherein applying comprises spraying or dip-coating the hydrophilic material upon at least the first surface.

5. The apparatus having a liner assembly prepared by the process comprising the steps of claim 1, further comprising irradiating the flexible elongate strip prior to bringing the first and second edges.

6. The apparatus having a liner assembly prepared by the process comprising the steps of claim 5, wherein irradiating comprising irradiating the flexible elongate strip with ultraviolet light.

7. The apparatus having a liner assembly prepared by the process comprising the steps of claim 1, further comprising heating the flexible elongate strip prior to joining the first and second edges.

8. The apparatus having a liner assembly prepared by the process comprising the steps of claim 1, wherein bringing the first and second edges comprises drawing the first and second edges over a mandrel such that the flexible elongate strip transitions into a tubular form.

9. The apparatus having a liner assembly prepared by the process comprising the steps of claim 8, further comprising applying a vacuum to the flexible elongate strip to stabilize the first and second edges relative to the mandrel.

10. The apparatus having a liner assembly prepared by the process comprising the steps of claim 1, wherein joining comprises fusing the first and second edges in a lap or butt joint.

11. The apparatus having a liner assembly prepared by the process comprising the steps of claim 1, wherein joining comprises applying an adhesive film to the first and second edges.

12. The apparatus having a liner assembly prepared by the process comprising the steps of claim 1, wherein joining comprises fusing a portion of the first and second edges to one another by applying heat to the portion.

13. The apparatus having a liner assembly prepared by the process comprising the steps of claim 1, further comprising cutting the formed flexible tubular liner to length.

14. An apparatus having a liner assembly prepared by a process comprising the steps of:
    coating at least a first surface of a flexible elongate strip having first and second edges with a hydrophilic material;
    irradiating the flexible elongate strip; drying the flexible elongate strip;
    bringing the first and second edges of the flexible elongate strip into proximity of one another;
    joining the first and second edges such that a flexible tubular liner is formed having the coated first surface formed as an inner surface of the flexible tubular liner; and
    joining said flexible tubular liner with a generally tubular outer sheath to form a liner assembly; and
    installing the liner assembly onto an elongate body having a tubular shape defining an internal lumen, wherein the tubular liner extends within the internal lumen and the outer sheath extends over an external surface of the elongate body.

15. The apparatus having a liner assembly prepared by the process comprising the steps of claim 14, wherein coating further comprises coating a second surface of the flexible elongate strip.

16. The apparatus having a liner assembly prepared by the process comprising the steps of claim 14, wherein coating comprises spraying or dip-coating the hydrophilic material upon at least the first surface.

17. The apparatus having a liner assembly prepared by the process comprising the steps of claim 14, wherein irradiating comprises irradiating the flexible elongate strip with ultraviolet light.

18. The apparatus having a liner assembly prepared by the process comprising the steps of claim 14, wherein drying comprises passing the flexible elongate strip through an oven.

19. The apparatus having a liner assembly prepared by the process comprising the steps of claim 14, wherein bringing the first and second edges comprises drawing the first and second edges over a mandrel such that the flexible elongate strip transitions into a tubular form.

20. The apparatus having a liner assembly prepared by the process comprising the steps of claim 19, further comprising applying a vacuum to the flexible elongate strip to stabilize the first and second edges relative to the mandrel.

21. The apparatus having a liner assembly prepared by the process comprising the steps of claim 14, wherein joining comprises fusing the first and second edges in a lap or butt joint.

22. The apparatus having a liner assembly prepared by the process comprising the steps of claim 14, wherein joining comprises applying an adhesive film to the first and second edges.

23. The apparatus having a liner assembly prepared by the process comprising the steps of claim 14, wherein joining comprises fusing a portion of the first and second edges to one another by applying heat to the portion.

24. The apparatus having a liner assembly prepared by the process comprising the steps of claim 14, further comprising cutting the formed flexible tubular liner to length.

* * * * *